US010894990B2

(12) United States Patent
Driscoll et al.

(10) Patent No.: US 10,894,990 B2
(45) Date of Patent: Jan. 19, 2021

(54) HIGH THROUGHPUT METHOD FOR IDENTIFICATION AND SEQUENCING OF UNKNOWN MICROBIAL AND EUKARYOTIC GENOMES FROM COMPLEX MIXTURES

(71) Applicant: Shoreline Biome, LLC, Farmington, CT (US)

(72) Inventors: Mark Driscoll, Wallingford, CT (US); Thomas Jarvie, Branford, CT (US)

(73) Assignee: Shoreline Biome, LLC, Farmington, CT (US)

( * ) Notice: Subject to any disclaimer, the term of this patent is extended or adjusted under 35 U.S.C. 154(b) by 0 days.

(21) Appl. No.: 15/596,366

(22) Filed: May 16, 2017

(65) Prior Publication Data

US 2017/0335410 A1   Nov. 23, 2017

Related U.S. Application Data

(60) Provisional application No. 62/337,507, filed on May 17, 2016.

(51) Int. Cl.
*C12Q 1/6888* (2018.01)
*C12Q 1/689* (2018.01)
*C12Q 1/6816* (2018.01)

(52) U.S. Cl.
CPC ........... *C12Q 1/6888* (2013.01); *C12Q 1/689* (2013.01); *C12Q 1/6816* (2013.01); *C12Q 2600/158* (2013.01)

(58) Field of Classification Search
CPC .... C12Q 1/6816; C12Q 1/6888; C12Q 1/689; C12Q 2600/158
USPC ................................................. 435/6.1, 91.2
See application file for complete search history.

(56) References Cited

U.S. PATENT DOCUMENTS

| | | | |
|---|---|---|---|
| 5,001,050 A | 3/1991 | Blanco et al. | |
| 5,198,543 A | 3/1993 | Blanco et al. | |
| 5,270,179 A | 12/1993 | Chatterjee | |
| 5,298,548 A | 3/1994 | Shiobara et al. | |
| 6,054,278 A | 4/2000 | Dodge | |
| 6,124,120 A | 9/2000 | Lizardi | |
| 6,280,949 B1 | 8/2001 | Lizardi | |
| 2005/0032654 A1 | 2/2005 | Mei et al. | |
| 2010/0069250 A1 | 3/2010 | White et al. | |
| 2012/0122737 A1 | 5/2012 | Sabot et al. | |
| 2012/0322112 A1 | 12/2012 | Pasloske et al. | |
| 2013/0157874 A1 | 6/2013 | Dowd | |
| 2014/0200146 A1 | 7/2014 | Xie et al. | |
| 2014/0378345 A1* | 12/2014 | Hindson .............. | C12O 1/6806 506/16 |
| 2015/0080266 A1 | 3/2015 | Volkmuth | |
| 2016/0040215 A1 | 2/2016 | Henn et al. | |
| 2017/0159108 A1 | 6/2017 | Budding et al. | |

FOREIGN PATENT DOCUMENTS

| | | |
|---|---|---|
| WO | 2013086201 A1 | 6/2013 |
| WO | 2015013214 A2 | 1/2015 |
| WO | WO2016061517 | 4/2016 |
| WO | WO2016130704 | 8/2016 |

OTHER PUBLICATIONS

May-Ping Lee et al., NAR, 37, D489-D493, published online Oct. 23, 2008.*
NCBI Insights., https://ncbiinsights.ncbi.nlm.nih.gov/2015/05/11/accessing-the-hidden-kingdom-fungal-its-reference-sequences-2/, pp. 1-4, May 11, 2015.*
Sharma et al., Barley Genetics Newsletter, vol. 32, shown as pp. 1-6, Oct. 2002.*
Schoch et al., PNAS, 109 (16): 6241-6246, Apr. 2012.*
Kuehn et al., 8 (4) e61959: 1-10, Apr. 2013.*
Aliotta, J. et al., Thermostable Bst DNA polymerase I lacks a 3'→5' proofreading exonuclease activity, Genetic Analysis: Biomolecular Engineering, Mar. 1996, pp. 185-195, vol. 12 Issues 5-6, Elsevier, Amsterdam, Netherlands.
Altschul, S. et al., Basic Local Alignment Search Tool, Journal of Molecular Biology, Oct. 5, 1990, pp. 103-410, vol. 215 Issue 3, Academic Press Limited.
Birnboim, H.C. et al., A rapid alkaline extraction procedure for screening recombinant plasmid DNA, Nucleic Acids Research, Nov. 24, 1979, pp. 1513-1523, vol. 7 No. 6.
Caporaso, J. et al., QIIME allows analysis of high-throughput community sequencing data, Nature Methods, May 2010, pp. 335-336, vol. 7 No. 5, Nature America, Inc.
Chatterjee, Deb et al., Cloning and overexpression of the gene encoding bacteriophage T5 DNA polymerase, Gene, Jan. 2, 1991, pp. 13-19, vol. 97 Issue 1, Elsevier, Amsterdam, Netherlands.
Deadman, R. et al., DNA purification through amplification: Use of Phi29 DNA polymerase to prepare DNA for genomic analyses, Amersham Biosciences Life Science News, 2004, pp. 14-15, vol. 18, Amersham Biosciences.
Desantis, T.Z. et al., Greengenes, a Chimera-Checked 16S rRNA Gene Database and Workbench Compatible with ARB, Applied and Environmental Microbiology, Jul. 2006, pp. 5069-5072, vol. 72 No. 7, American Society for Microbiology.
Drancourt, Michel et al., 16S Ribosomal DNA Sequence Analysis of a Large Collection of Environmental and Clinical Unidentifiable Bacterial Isolates, Journal of Clinical Microbiology, Oct. 2000, pp. 3623-3630, vol. 38 No. 10, American Society for Microbiology.
Yuan, Sanqing et al., Evaluation of Methods for the Extraction and Purification of DNA from the Human Microbiome, PLoS One, Mar. 23, 2012, pp. 1-13, vol. 7 No. 3.

(Continued)

*Primary Examiner* — Cynthia B Wilder
(74) *Attorney, Agent, or Firm* — Wiggin and Dana LLP; Anthony D. Sabatelli

(57) ABSTRACT

Disclosed are methods for screening biological samples for the presence unknown microbes, such as bacteria and archaea or unknown eukaryotes using rRNA gene sequences or other highly conserved genetic regions, across multiple biological samples using a unique sequence tag (barcode) corresponding to the sample. The screening process tracks the unknown microbe or eukaryote in a diluted sample where the DNA has been prepared using whole genome amplification. The whole genome of the unknown microbe or eukaryote is then sequenced and assembled.

25 Claims, 1 Drawing Sheet

(56) References Cited

OTHER PUBLICATIONS

Raghunathan, Arumugham et al., Genomic DNA Amplification from a Single Bacterium, Applied and Environmental Microbiology, Jun. 2005, pp. 3342-3347, vol. 71 No. 6, American Society for Microbiology.

Jacobsen, Henning et al., The N-Terminal Amino-Acid Sequences of DNA Polymerase I from *Escherichia coli* and of the Large and the Small Fragments Obtained by a Limited Proteolysis, Eur. J. Biochem, 1974, pp. 623-626, vol. 45.

Matsumoto, Kouji, et al., Primary structure of bacteriophage M2 DNA polymerase: conserved segments within protein-priming DNA polymerases and DNA polymerase I of *Escherichia coli*, Gene, 1989, pp. 247-255, vol. 84, Elsevier Science Publishers B.V.

Marcy, Yann et al., Dissecting biological "dark matter" with single cell genetic analysis of rare and uncultivated TM7 microbes from the human mouth, Applied Physical Sciences, Microbiology, Jul. 17, 2007, pp. 11889-11894, vol. 104 No. 29, Proceedings of the National Academy of Sciences of the United States of America.

Jung, Guhung et al., Bacteriophage PRD1 DNA polymerase: Evolution of DNA polymerases, Biochemistry, Dec. 1987, pp. 8287-8291, vol. 84, Proceedings of the National Academy of Sciences of the United States of America.

Kong, Huimin et al., Characterization of a DNA Polymerase from the Hyperthermophile Archaea Thermococcus litoralis, The Journal of Biological Chemistry, Jan. 25, 1993, pp. 1965-1975, vol. 268 No. 3, The American Society for Biochemistry and Molecular Biology.

Lawyer, Frances et al., Isolation, Characterization and Expression in *Escherichia coli* of the DNA Polymerase Gene from Thermus aquaticus, The Journal of Biological Chemistry, Apr. 15, 1989, pp. 6427-6437, vol. 264 No. 11, The American Society for Biochemistry and Molecular Biology.

Mackenzie, Brett et al., Evaluating variation in human gut microbiota profiles due to DNA extraction method and inter-subject differences, Frontiers in Microbiology, 2015, pp. 1-11, vol. 6 Article 130.

Zhu, Weiguo et al., Purification and characterization of PRD1 DNA polymerase, Biochimica et Biophysica Acta, 1994, pp. 267-276, vol. 1219, Elsevier Sciences B.V.

Walker, G. et al., Detection of Mycobacterium tuberculosis DNA with thermophilic strand displacement amplification and fluorescence polarization, Clinical Chemistry, 1996, pp. 1604-1608, vol. 42 Issue 10.

Vetrovsky, Tomas et al., The Variability of 16S rRNA Gene in Bacterial Genomes and Its Consequences for Bacterial Community Analyses, PLoS One, Feb. 27, 2013, pp. 1-10, vol. 8 Issue 2.

Schloss, Patrick et al., Introducing mothur: Open-Source, Platform-Independent, Community-Supported Software or Describing and Comparing Microbial Communities, Applied and Environmental Microbiology, Dec. 2009, pp. 7537-7541, vol. 75 No. 23, American Society for Microbiology.

Quast, Christian, The SILVA ribosomal RNA gene database project: improved data processing and web-based tools, Nucleic Acids Research, 2013, pp. D590-D596, vol. 41.

Pinard, Robert et al., Assessment of whole genome amplification-induced bias through high-throughout, massively parallel whole genome sequencing, BMC Genomics, 2006, pp. 1-21, vol. 7 No. 216, Biomed Central Ltd.

PCT International Search Report and Written Opinion in related PCT Application PCT/US16/65700, dated Apr. 28, 2017, 10 pages.

PCT International Search Report and Written Opinion in related PCT Application PCT/US17/33008, dated Aug. 14, 2017, 8 pages.

Dietmaier, W. et al, Multiple mutation analyses in single tumor cells with improved whole genome amplification, American Journal of Pathology, 1999, pp. 83-95, vol. 154 Issue 1, Elsevier.

Zhang, L. et al., Whole genome amplification from a single cell: Implications for genetic analysis, Genetics, Jul. 1992, pp. 5847-5851, vol. 89 Issue 1, Proceedings of the National Academy of Sciences of the United States of America.

Telenius, H. et al., Cytogenetic analysis by chromosome painting using dop-pcr amplified flow-sorted chromosomes, Genes, Chromosomes & Cancer, Apr. 1992, pp. 257-263, vol. 4 Issue 3, Wiley.

Dean, F. et al., Rapid Amplification of Plasmid and Phage DNA Using Phi29 DNA Polymerase and Multiply-Primed Rolling Circle Amplification, Genome Research, 2001, pp. 1095-1099, vol. 11 Issue 6, Cold Spring Harbor Laboratory Press.

Blainey, P.C., The future is now: single-cell genomics of bacteria and archaea, FEMS Microbiology Review, May 2013, pp. 407-427, vol. 37 Issue 3.

Lasken, R. et al., Recent advances in genomic DNA sequencing of microbial species from single cells, Nature Reviews Genetics, Aug. 2014, pp. 577-584, vol. 15.

Parameswaran, Poornima et al. A pyrosequencing-tailored nucleotide barcode design unveils opportunities for large-scale sample multiplexing, Nucleic Acids Research, Oct. 2007, vol. 35, Issue 19.

European Paent Office, Extended European Search Report, European Patent Application No. 17800055.0/1118, dated Nov. 13, 2019.

Petrosino, J.F. et al., Metagenomic Pyrosequencing and Microbial Identification, Clinical Chemistry, 2010, 55:5, pp. 856-866.

\* cited by examiner

Step 1: Screen samples for unknown bacteria using the Shoreline Biome DNA Preparation and Amplicon Kits. Sequencing the rRNA gene region of unknown bacteria typically reveals previously unknown unique DNA sequence that can be used as an ID, called USID

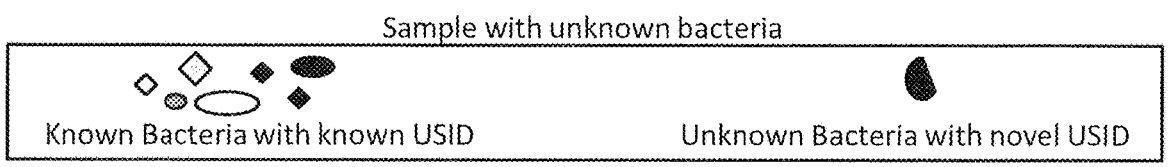

Step 2: Isolate microbe of interest into individual container by diluting sample and distributing aliquots such that each well contains 0-1 microbe

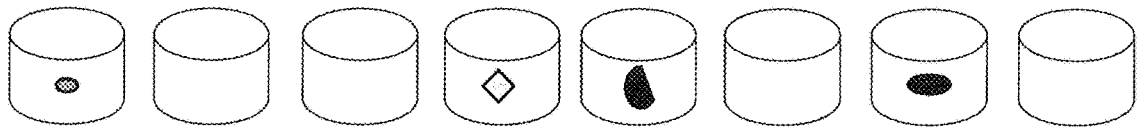

Step 3: Purify/amplify DNA in diluted samples using Whole Genome Amplification. Store the resulting amplified genomic DNA (gDNA) for steps 4 and 5

Step 4: Identify well(s) containing the USID from the unknown bacterium. This can be accomplished by sequencing, restriction digestion, or gel sizing of a PCR product targeting the USID sequence

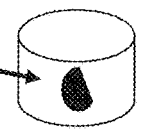

Step 5: Sequence and assemble the gDNA from the well with the unknown bacterium.

HIGH THROUGHPUT METHOD FOR IDENTIFICATION AND SEQUENCING OF UNKNOWN MICROBIAL AND EUKARYOTIC GENOMES FROM COMPLEX MIXTURES

CROSS-REFERENCE TO RELATED APPLICATIONS

This application claims the benefit under 35 U.S.C. § 119(e) to U.S. Provisional Application No. 62/337,507, filed May 17, 2016, the entire contents of which are incorporated herein by reference in their entirety.

FIELD OF THE DISCLOSURE

Disclosed are methods for screening biological samples for the presence of unknown microbes, including prokaryotes (bacteria and archaea) and eukaryotes using ribosomal RNA gene regions, across multiple biological samples using a Unique Sequence IDentifier (USID) corresponding to the microbe. The screening process tracks the unknown microbe or eukaryote in a diluted sample where the DNA has been prepared using whole genome amplification. The whole genome of the unknown microbe or eukaryote is then sequenced and assembled.

BACKGROUND

Unknown bacteria and archaea typically exist in diverse communities that may consist of hundreds or thousands of different strains, and each strain may comprise a small or large part of a given population. In addition, most bacteria and archaea cannot be cultured by any known means. Shotgun sequencing of all the bacteria and archaea that constitute a complex microbiome results in mostly wasted sequence data that comes primarily from the most frequent and best understood bacteria and archaea. For these reasons, identification, isolation and sequencing of unknown microbes from biological samples is impractical or impossible for most investigators. Disclosed herein are rapid and simple methods for identification, quantification, tracking, isolation, and sequencing of unknown microbes that can be applied to any biological sample containing known and unknown microbes. The disclosed methods may be used for isolation and sequencing of microbes in human samples, or for any sample of microbes from any source. Because the disclosed methods do not require microbes to be cultured to obtain sufficient material for sequencing, they can be used to sequence microbes that are considered unculturable.

Methods of preparing DNA, amplifying rRNA gene sequences and sample barcode tagging are described in U.S. patent application Ser. No. 15/372,588, which is incorporated by reference herein in its entirety.

DNA amplification techniques are typically employed when DNA sources are limiting, with the goal of producing enough DNA for study. Some of these amplification techniques include I-PEP-PCR (Dietmaier, W., Hartmann, A., Wallinger, S., Heinmoller, E., Kerner, T., Endl, E., Jauch, K. W., Hofstadter, F., and Ruschoff, J. *Multiple mutation analyses in single tumor cells with improved whole genome amplification*, Am. J. Pathol. (1999) 154: 83-95), PEP-PCR (Zhang, L., Cui, X., Schmitt, K., Hubert, R., Navidi, W., and Arnheim, N. *Whole genome amplification from a single cell: Implications for genetic analysis*. Proc. Natl. Acad. Sci. (1992) 89: 5847-5851), phi29 amplification (Lizardi, Paul M. Multiple displacement amplification, U.S. Pat. No. 6,280,949, issued Aug. 28, 2001), and Degenerate Oligonucleotide Primer (DOP) PCR (Telenius, H., Ponder, B., Tunnacliffe, A., Pelmear, A., Carter, N., Ferguson-Smith, M., Behmel A., Nordenskjöld, M., and Pfragner, R. *Cytogenetic analysis by chromosome painting using dop-pcr amplified flow sorted chromosomes*, Genes, Chromosomes and Cancer 4(3) (1992): 257-263). Although it is typically used for whole genome amplification reactions, phi29 polymerase is also useful because it can function in the presence of contaminants that strongly inhibit other polymerases. Phi29 DNA polymerase is commercially available from vendors such as Thermo Fisher Scientific (Waltham, Mass.) and New England BioLabs (Ipswich, Mass.). U.S. Pat. No. 6,280,949 is incorporated by reference herein in its entirety.

Barcoding individual samples with specific DNA tags allows many samples to be combined for sequencing, streamlining the workflow, decreasing time to result, and reducing costs. DNA barcoding for sample identification has been described for the very first of the next generation sequencing (NGS) platforms, the GS 20, in 2007 (Parameswaran P, Jalili R, Tao L, et al. *A pyrosequencing-tailored nucleotide barcode design unveils opportunities for large-scale sample multiplexing*. Nucleic Acids Research. 2007; 35(19):e130. doi:10.1093/nar/gkm760). Since that time, barcoding strategies have been made commercially available by Illumina (San Diego, Calif.), Pacific Biosciences (Menlo Park, Calif.), and Thermo Fisher Scientific (Waltham, Mass.) sequencing platforms.

Rolling circle amplification protocols, materials, and methods using phi29 polymerase are described in Dean, et al. (Dean F. B., Nelson, J. R., Giesler, T. L., and Lasken, R. S. *Rapid Amplification of Plasmid and Phage DNA Using Phi29 DNA Polymerase and Multiply-Primed Rolling Circle Amplification*. Genome Research, (2001), 11(6), 1095-1099). Whole genome amplification using phi29 DNA polymerase is described in U.S. Pat. No. 6,124,120, Paul Lizardi, issued Sep. 26, 2000, titled "Multiple displacement amplification". U.S. Pat. No. 6,124,120 is incorporated by reference herein in its entirety.

Advantages of using phi29 as a DNA purification technique were outlined in R. Deadman, and K. Jones. *DNA purification through amplification: Use of Phi29 DNA polymerase to prepare DNA for genomic analyses*, Amersham Biosciences Life Science News, (18), (2004): 14-15, which highlights the use of phi29 amplification for sequencing of single clones using Sanger sequencing, and mentions that "amplified DNA has been successfully used in many applications including PCR (simple, multiplex and real-time), SNP genotyping (Third Wave Invader™ assay (Third Wave Technologies, Inc., Madison, Wis.), MegaBACE™ SNuPe™ genotyping kit (GE Healthcare Life Sciences, Pittsburgh, Pa.), Affymetrix™ GeneChip™ HuSNP™ chip (Affymetrix, Santa Clara, Calif.), Pyrosequencing, STR and SSR genotyping, comparative genomic hybridization (CGH), cloning and library construction, heteroduplex analysis, slot and dot blots, yeast-2-hybrid systems, and microarray analysis". This article was published by the commercial vendor Amersham before the launch of Next-Generation Sequencing Systems.

Other polymerases are known in the art, including Thermostable Bst DNA polymerase exonuclease (−) large fragment (Aliotta J. M., J. J. Pelletier, J. L. Ware, L. S. Moran, J. S. Benner, and H. Kong. *Thermostable Bst DNA polymerase I lacks a 3' to 5' proofreading exonuclease activity*. Genet. Anal. 12:185-195, (1996)), Exonuclease (−) Bca DNA polymerase (Walker, G. T. and Linn, C. P. *Detection of Mycobacterium tuberculosis DNA with thermophilic strand* displacement amplification and fluorescence polarization. Clinical Chemistry 42:1604-1608 (1996)), Thermus aquaticus YT-1 polymerase (Lawyer, F. C., Stoffel, S., Saikit, R. K., Myambo, K., Drummond, R., and Gelfand. D. H. Isolation, Characterization, and Expression in Escherichia coli of the DNA Polymerase Gene from Thermus aquaticus. J. Biol. Chem., 264, 6427-6437 (1989)), Phage M2 DNA polymerase (Matsumoto, K., Takano, H, Kim, C. I, and Hirokawa H. Primary structure of bacteriophage M2 DNA polymerase: conserved segments within protein-priming DNA polymerases and DNA polymerase I of Escherichia coli. Gene 84:247-255 (1989)), Phage PRD1 DNA polymerase (Jung, G., Leavitt M. C., Hsieh J-C., Ito, J. Bacteriophage PRD1 DNA polymerase: evolution of DNA polymerases. Proc. Natl. Acad. Sci. U.S.A. 84:8287-8291 (1987)), Exonuclease (−)VENT DNA polymerase (Kong, H., Kucera, R. B., and Jack W. E. Characterization of a DNA polymerase from the hyperthermophile archaea Thermococcus litoralis. Vent DNA polymerase, steady state kinetics, thermal stability, processivity, strand displacement, and exonuclease activities. J. Biol. Chem. 268:1965-1975 (1993)), Klenow fragment of DNA polymerase I (Jacobsen, H., Klenow, H., and Overoaard-Hansen, H. The N-Terminal Amino-Acid Sequences of DNA Polymerase I from Escherichia coli and of the Large and the Small Fragments Obtained by a Limited Proteolysis. Eur J. Biochem. 45:623-627 (1974)), T5 DNA polymerase (Chatterjee D. K., Fujimura R. K., Campbell J. H., Gerard G. F. Cloning and overexpression of the gene encoding bacteriophage T5 DNA polymerase. Gene 97:13-19 (1991)) U.S. Pat. No. 5,270,179 and PRD1 DNA polymerase (Zhu, W; Ito, J.: Purification and characterization of PRD1 DNA polymerase. Biochimica et Biophysica Acta 1219:267-276 (1994)).

A publication by Robert Pinard, et al. (Pinard, R., et al., "Assessment of whole genome amplification-induced bias through high-throughput, massively parallel whole genome sequencing" (BMC Genomics (7):216(2006)) indicated that the bias across the genome for certain sequences was up to 100 fold, implying that there are severe limitations on the utility of the method for DNA purification.

In a publication demonstrating amplification of DNA from a single cell for 16S rRNA amplicon sequencing, the inventor Mark Driscoll was an author because his group performed the work at Molecular Staging in 2004, prior to the introduction of Next Generation Sequencing technology. The publication contains useful discussion of bias as it relates to number of cells in starting material. (Ragunathan, et al., Genomic DNA Amplification from a Single Bacterium, Appl. Environ. Microbiol. June 2005, vol. 71 no. 6 3342-3347.) See also, Blainey, P. C., The future is now: single-cell genomics of bacteria and archaea. FEMS Microbiol Rev 37 (2013) 407-427, and Lasken, R., and McLean, J., Recent advances in genomic DNA sequencing of microbial species from single cells. Nat Rev Genet. 2014 September; 15(9): 577-584.

BRIEF SUMMARY

Samples of interest may contain mixtures of prokaryotes or eukaryotes, both known and unknown. An example is a microbiome sample that contains mixtures of known and unknown microbes. Microbes can be identified by their DNA sequence. An efficient method for scanning many microbial samples at once is to prepare barcoded DNA amplicons targeting the rRNA genes from each sample, and pool the barcoded samples for DNA sequencing in a high throughput format. Sequencing the rRNA genes from the microbes will reveal previously unsequenced genetic regions (Unique Sequence IDs, or USIDs) corresponding to novel bacteria. The USIDs can be used to detect individual unknown bacteria, which can be isolated from the original sample, and their genomic DNA can be amplified by Whole Genome Amplification for genome sequencing.

Disclosed herein are methods for identifying an unknown microbe in a biological sample, including: (a) selecting one or more biological samples having an unknown microbe, wherein the selecting includes deoxyribonucleic acid (DNA) sequencing of one or more polymerase chain reaction (PCR) target sequences from whole genome DNA of the biological samples, so as to identify one or more Unique DNA sequence Identifiers (USID) of the unknown microbe; (b) diluting the biological sample having the unknown microbe selected in step (a) into a high throughput format so as to enable whole genome amplification and sequencing of single microbes in the biological sample; (c) amplifying whole genome DNA from the single microbes in step (b) in a high throughput format; (d) PCR amplifying the USID sequences identified in step (a) from the genomic DNA in step (c) and detecting the presence or absence of the USID of the unknown microbe in each sample from step (c), and (e) conducting DNA sequencing on the whole genome amplified DNA of the unknown microbe identified in step (d), and assembling the DNA sequences into the genome of the unknown microbe. In some embodiments, the methods are conducted to identify more than one unknown microbe in a biological sample.

In some embodiments, the one or more USID sequences are highly conserved gene sequences, or portions or fragments of such gene sequences, for example survival genes or other genes that are conserved in over 70% of prokaryotes. In some embodiments, the USID sequence is selected from the group consisting of: a bacterial or eukaryotic ribosomal ribonucleic acid (rRNA) gene, human leukocyte antigen (HLA), microbial toxin producing genes, microbial pathogenicity genes, microbial plasmid genes, human immune system genes, immune system components, 16S rRNA gene sequence, 18S rRNA gene sequence, 26S rRNA sequence, Internally Transcribed Spacer 1 (ITS1), Internally Transcribed Spacer 2 (ITS2), heat shock protein 65 (HSP65), rpoB, recA or any combination thereof, including portions or fragments thereof. In some embodiments, the USID sequence is a rRNA gene sequence and an ITS sequence, or portions or fragments thereof.

In some embodiments, the diluting in step (b) results in one microbe in at least one well of a multiwell plate. In some embodiments, the step of detecting the presence or absence of the USID comprises DNA sequencing or restriction digestion or both.

In some embodiments, the high throughput format is selected from the group consisting of: at least six samples, at least twenty-four samples, at least forty-eight samples, or at least ninety-six samples. In some embodiments, the high throughput format contains ninety-six samples.

In some embodiments, the biological sample is any material or fluid obtained from a human, animal, plant, or the environment. In some embodiments, the biological sample is a crude biological sample or a partially-purified biological sample. In some embodiments, the biological sample is selected from the group consisting of: feces, cell lysate, tissue, blood, tumor, tongue, tooth, buccal swab, phlegm, mucous, wound swab, skin swab, vaginal swab, biological material or biological fluid. In some embodiments, the biological sample is a microbiome sample.

In some embodiments, the DNA sequencing in step (e) is selected from the group consisting of: a next-generation sequencing (NGS) method, Sanger sequencing or other sequencing methods. In some embodiments, the assembling in step (e) employs computer implemented methods.

In some embodiments, the methods disclosed herein are performed to identify one or more unknown eukaryotes in a biological sample. In such embodiments, the USID sequences are selected from highly conserved eukaryotic gene sequences, or portions or fragments of such gene sequences, for example the 18s rRNA gene and related eukaryotic rRNA genes.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention will be apparent from the following detailed description taken in conjunction with the accompanying drawings.

FIG. 1 depicts an example of an embodiment of the present invention as described herein.

DETAILED DESCRIPTION

Microbes, such as bacteria and archaea, can be identified using their ribosomal RNA (rRNA) gene sequence, which is required for the survival of all prokaryotic microbes. Individual species of bacteria and archaea have characteristic DNA variations in the rRNA gene that serve as identifiers, fingerprints, or Unique Sequence IDentifiers (USID) for that species. The methods described herein enable comprehensive generation of USIDs for each of the microbes in a sample, at high resolution, using amplicons spanning sections of the rRNA gene, using, for example, the Shoreline Biome EXT-16S DNA Purification and PCR Amplification Kit, which generates USID sequences in the Internally Transcribed Spacer Region between the 16S and 23S rRNA genes in bacteria and archaea. A subset of samples (referred to as "sub-samples") may contain one or more previously unknown microbes with novel USIDs that can be identified and tracked using their novel amplicon DNA sequence. These unknown microbes are of significant interest to investigators studying the microbiome. The general methods described herein can also be used to track rRNA gene sequences to identify novel eukaryotes, such as fungi, from biological samples.

Disclosed herein are methods for identifying, isolating and sequencing unknown cells (or microbes) in a biological sample. The term "unknown," as used herein, means a cell or microbe or other target of interest that is not known to be present in a biological sample or has not been confirmed as present in a biological sample. The steps of the methods include identifying and selecting biological samples having unknown bacteria that contain novel USID DNA sequences; diluting the selected biological sample into a high throughput format so as to enable whole genome amplification of single cells (or microbes) in a sub-sample of the biological sample; amplifying whole genome DNA from the single cells or microbes in a high throughput format; performing PCR amplification on the whole genome amplified DNA, for example PCR of the rRNA sequences from the genomic DNA, wherein the target rRNA amplicon sequence contains a recognizable unique sequence element (USID) that is simultaneously tagged with a unique DNA code corresponding to the sample; either digesting the amplicon with restriction enzymes that cut the USID into discrete fragments so that the presence of the unknown's USID in that sample can be recognized by a pattern on a gel, or pooling and sequencing the rRNA amplicons to identify the samples containing the USID from the unknown of interest; and conducting DNA sequencing on the samples containing the whole genome of the unknown single cell (or microbe) of interest from and assembling the DNA sequences into the genome of the single cell (or microbe).

In some embodiments, the step of selecting biological samples having unknown bacteria with novel USID DNA sequences includes (i) purifying genomic DNA from biological samples in a high throughput format; and (ii) for each biological sample, PCR amplifying target DNA sequences (e.g., rRNA gene) from the genomic DNA from step (i), wherein each target DNA sequence has a Unique Sequence Identifier (USID) associated with the cell (or microbe) of interest, and sequencing the PCR target DNA sequences so as to identify biological samples having an unknown target DNA sequence which can be selected for subsequent steps of the method. A commercially available kit, for example the Shoreline Biome EXT-16S DNA Purification and PCR Amplification Kit, can be used for this purpose.

In some embodiments, the step of diluting the selected biological sample results in a sub-sample of one cell (or microbe) in at least one well of a multiwell plate. In some embodiments, the diluting results in a sub-sample of one or more cells (or microbes) in at least one well of a multiwell plate. In some embodiments, the diluting results in a sub-sample of one, two, three, four, five, six, seven, eight, nine or ten cells (or microbes) in at least one well of a multiwell plate.

In some embodiments, the methods are used to identify and sequence an unknown organism or cell selected from the group consisting of: multicellular organisms, unicellular organisms, prokaryotes, eukaryotes, microbes, bacteria, archaea, protozoa, algae and fungi.

In some embodiments, the high throughput format is selected from the group consisting of: at least six samples, at least twenty-four samples, at least forty-eight samples, or at least ninety-six samples. Biological samples may be transferred to multi-well plates, for example 96, 384 or 1096 well plates, or to microreactors contained in microfluidics devices that integrate one or more laboratory functions.

In some embodiments, the biological sample is selected from the group consisting of: feces, cell lysate, tissue, blood, tumor, tongue, tooth, buccal swab, phlegm, mucous, wound swab, skin swab, vaginal swab, or any other biological material or biological fluid originally obtained from a human, animal, plant, or environmental sample, including raw samples, complex samples, mixtures, and microbiome samples. In some embodiments, the biological sample is crude or partially-purified. A "crude biological sample" as used herein, means a sample that has not been processed, altered or treated relative to its natural state. A "partially-purified biological sample" as used herein, means a sample that has been processed, altered or treated relative to its natural state but still contains contaminants or impurities.

In some embodiments, the method further comprises a step of cell lysis or cell membrane solubilization to open the cells to make the DNA accessible for amplification by a polymerase. Methods of cell lysis and cell membrane solubilization are known in the art, for example, alkaline lysis. (Birnboim, H. C. and J. Doly, J., *A rapid alkaline extraction procedure for screening recombinant plasmid DNA, Nucl. Acids Res.* (1979) 7 (6): 1513-1523). In some embodiments of the methods described herein, cells in the crude sample are lysed an alkaline solution consisting of 0.2M KOH. Either higher or lower concentrations of KOH may be used. Other bases, such as NaOH, may be substituted. In some embodiments, a detergent, such as sodium dodecyl sulfate, may be used to solubilize cell membranes and proteins. In some embodiments, the method comprises one or more reagents to lyse cells or solubilize cell membranes so as to release DNA from cells in the sample, including but not limited to, alkaline reagents or bases, for example potassium hydroxide or sodium hydroxide, or a detergent, such as sodium dodecyl sulfate, or an enzyme, such as lysozyme.

In some embodiments, purification of DNA involves cell lysate that is used directly in PCR.

In some embodiments, purification of DNA involves cell lysate that is subjected to further DNA purification methods know in the art, such as various DNA miniprep methods, alcohol precipitation, or commercially available methods such as column purification.

Whole genome amplification steps may include thermocycling or isothermal protocols, or a combination thereof. Whole genome amplification primers may include random primers or target specific primers, or combinations thereof. In some embodiments, purification of DNA involves the amplification of whole genome DNA using a DNA polymerase capable of producing high yields of purified DNA from a crude or partially purified biological sample. In some embodiments, the polymerase is a strand displacement DNA polymerase. In some embodiments, the polymerase is phi29 DNA polymerase (NCBI Accession No: ACE96023, U.S. Pat. Nos. 5,198,543 and 5,001,050, inventors Luis Blanco, Antonio Bernad, Margarita Salas). In some embodiments, the polymerase is selected from the group consisting of: phi29, Thermostable Bst DNA polymerase exonuclease (−) large fragment, Exonuclease (−) Bca DNA polymerase, *Thermus aquaticus* YT-1 polymerase, Phage M2 DNA polymerase, Phage PRD1 DNA polymerase, Exonuclease (−)VENT DNA polymerase, Klenow fragment of DNA polymerase I, T5 DNA polymerase, and PRD1 DNA polymerase.

In some embodiments, the amplification of target DNA sequences employs a polymerase chain reaction (PCR). In some embodiments, PCR primers may contain identifying 'barcode' sequences that can be used to determine sample identity after pooling with other samples and sequencing. DNA barcodes can be selected to be of sufficient length to generate the desired number of barcodes with sufficient variability to account for common sequencing errors, generally ranging in size from about 3 to about 20 bases, but may be longer or shorter. In some embodiments, the barcode has a length of 2 bases, 3 bases, 4 bases, 5 bases, 6 bases, 7, bases, 8 bases, 9 bases 10 bases, 11 bases 12 based 13 bases, 14 bases, 15 bases, 16 bases, 17 bases, 18 bases, 19 bases, 20 bases, 25 bases, 30 bases or 35 bases. The target specific PCR sequences for the forward and reverse PCR primers can be specific for any DNA sequence, in coding or non-coding regions of a target genome, plasmid, or organelle. In some embodiments, the target USID DNA sequence is an amplicon, or targeted gene sequence, such as bacterial or eukaryotic rRNA genes, human HLA, microbial toxin producing genes, microbial pathogenicity genes, microbial plasmid genes, human immune system genes, immune system components, a 16S rRNA gene sequence, 18S rRNA gene sequence, 26S rRNA sequence, other genes such as ITS1, ITS2, HSP65, rpoB, or recA, and other variable genetic regions of non-human organisms. In some embodiments, the target USID sequence encompasses one or more gene sequences or portions thereof. In some embodiments, the target USID sequence encompasses the 16S rRNA gene, the adjacent Internally Transcribed Spacer (ITS) region, and part of the 23S rRNA gene. In some embodiments the target USID sequence encompasses the 16S rRNA gene. In some embodiments, the target USID sequence consists of all or part of each of the 16S rRNA gene, the ITS region, the 23S rRNA gene.

The high throughput sequencing method can be any method, with high throughput generally meaning greater than 1000 reads per run. In some embodiments, the high throughput DNA sequencing is a next-generation sequencing (NGS) method. In some embodiments, the DNA sequencing method is Sanger sequencing or other low throughput sequencing methods. Sanger sequencing is a method of DNA sequencing based on the selective incorporation of chain-terminating dideoxynucleotides by DNA polymerase during in vitro DNA replication. In some embodiments, assembling DNA sequences into a genome employs computer implemented methods.

EXAMPLE

FIG. 1 depicts an example of an embodiment of the present invention used to identify, isolate, and sequence an unknown microbe in a biological sample without having to culture the organism (Steps 1-5, described below). In Step 1, a number (for example 96) biological samples are screened for novel microbes using DNA sequencing methods. The screening process in this embodiment includes lysis of cells and purification of cellular genomic DNA (gDNA) from the sample, amplification of the rRNA gene target region(s) while adding DNA barcodes to each sample so that the 96 samples can be pooled for simultaneous sequencing. The process as described in this example can be carried out using, for example, Shoreline Biome DNA Preparation and Amplicon Kits. The amplified barcoded rRNA sequences in each sample can be screened for the presence of unknown sequences that are contained in unknown microbes.

Step 1.

The rRNA sequence data will reveal the presence of unknown microbes in the samples. Although samples may be sequenced together, the reads that originated with each sample can be identified by reading the barcode attached during PCR of the target region. The PCR target region is selected such that all microbes will generate a PCR product, for example, the target may be in the 16S, 23S, ITS, or similar genespace that is required for survival, and therefore conserved. Part or all of the sequenced PCR target can become a USID for each organism in the sample. Previously unknown USIDs are identified by mapping the DNA sequencing results to genomic databases such as GenBank. In this example, a sample with an unknown rRNA gene unique sequence ID (USID) in the ITS region between the 16S and 23S rRNA genes corresponding to an unknown microbe is identified as the sample of interest.

Step 2.

In one embodiment, an aliquot of a sample of interest (containing an unknown USID sequence) is diluted into wells such that only one microbe (or cell) is in each well. This is especially useful in the case of fecal microbiomes, where there is a very low percentage (~1%) of host eukaryotic cells. Since eukaryotic genomes are approximately 1000× larger than most bacterial genomes, limiting the number of eukaryotic cells is important for downstream shotgun sequencing. The methods can also be used when the sample of interest is diluted to a limited number of microbes per well, for example, ten or fewer microbes per well.

Depending upon the prevalence of the unknown microbes and contaminating eukaryotic cells in the sample, it may make more sense from a cost, speed, and efficiency standpoint to either target one cell per well (if the unknown microbes are common and eukaryotic cells are also common) or multiple cells per well (if the unknown microbes are uncommon, and eukaryotic cells are also uncommon).

Step 3.

The microbe(s) in each well are subjected to high throughput whole genome amplification (shown here in 8 wells of a multiwell plate) in parallel to produce high yields of purified DNA, for example using alkaline, detergent, or enzymatic lysis to open cells followed by phi29 or Bst DNA polymerase amplification methods.

Step 4:

A small amount of each whole genome amplified sample is analyzed for the presence of the USID corresponding to the unknown microbe. The USID sequence is amplified by PCR using primers specific for the USID. The presence of a cell in each diluted well is determined by gel sizing of the PCR product. Wells with no PCR product can be ignored for subsequent steps. Samples with PCR product corresponding to the expected size of the USID must have contained a cell with a USID similar in size to the target organism, and are selected for testing in subsequent steps. The USID base sequence can be determined by DNA sequencing and/or restriction digestion using methods known in the art. DNA sequencing will determine the full sequence of the target region PCR USID product, but can be slow and expensive. Restriction digestion of the target region PCR USID product is performed with one or more restriction enzymes that cut the desired target at specific locations, resulting in specific banding patterns on a gel. The banding patterns can be compared to those expected based on the USID sequence to identify wells containing the microbe of interest.

Step 5.

Whole genome amplified DNA from the well with the unknown organism/USID genetic sequence is subjected to shotgun sequencing to sequence the full genome of the unknown microbe. In the embodiment where the dilution was performed to generate one microbe per well, only the unknown microbe of interest is expected to be present. In an embodiment where more than one microbe is present, reads mapping only to known microbe(s) can be discarded prior to assembly, or an assembly can be done de novo, on all DNA within the multi-microbe mixture, to reconstruct the separate genomes of each microbe in the mix.

All patent applications, patents and other publications cited herein are incorporated by reference in their entirety. One or more embodiments of the present invention have been described. Nevertheless, it will be understood that various modifications may be made without departing from the spirit and scope of the invention. Accordingly, other embodiments are within the scope of the following claims.

What is claimed is:

1. A method for identifying an unknown microbe in a biological sample, comprising:
    a. selecting one or more biological samples having an unknown microbe, wherein the selecting comprises deoxyribonucleic acid (DNA) sequencing of one or more polymerase chain reaction (PCR) target sequences from whole genome DNA of the biological samples, so as to identify one or more unknown Unique DNA sequence Identifiers (USID) of the unknown microbe, wherein the (PCR) target sequence comprises one or more rRNA gene sequences and an Internally Transcribed Spacer (ITS) sequence, or a portion thereof comprising both the one or more rRNA gene sequences and the ITS sequence; wherein the identification is performed by comparing the DNA sequence results to a genomic database to ascertain whether the USID is known or unknown;
    b. diluting the biological sample having the unknown microbe selected in step (a) into a high throughput format so as to enable whole genome amplification and sequencing of single microbes in the biological sample;
    c. amplifying whole genome DNA from the single microbes in step (b) in a high throughput format;
    d. PCR amplifying the unknown USID sequences identified in step (a) from the genomic DNA in step (c) and detecting the presence of the unknown USID of the unknown microbe in each sample from step (c); and
    e. conducting DNA sequencing on the whole genome amplified DNA of the unknown microbe identified in step (d), and assembling the DNA sequences into the genome of the unknown microbe; and
    f. identifying the unknown microbe based on the DNA sequence of the unknown USID.

2. The method of claim 1, wherein the diluting in step (b) results in one microbe in at least one well of a multiwell plate.

3. The method of claim 1, wherein the high throughput format is selected from the group consisting of: at least six samples, at least twenty-four samples, at least forty-eight samples, or at least ninety-six samples.

4. The method of claim 3, wherein the high throughput format contains ninety-six samples.

5. The method of claim 1, wherein the biological sample is any material or fluid obtained from a human, animal, plant, or the environment.

6. The method of claim 5, wherein the biological sample is a crude biological sample or a partially-purified biological sample.

7. The method of claim 6, wherein the biological sample is selected from the group consisting of: feces, cell lysate, tissue, blood, tumor, tongue, tooth, buccal swab, phlegm, mucous, wound swab, skin swab, vaginal swab, biological material or biological fluid.

8. The method of claim 6, wherein the sample is a microbiome sample.

9. The method of claim 1, wherein the DNA sequencing in step (e) is selected from the group consisting of: a next-generation sequencing (NGS) method, Sanger sequencing or other sequencing methods.

10. The method of claim 1, wherein the assembling in step (e) employs computer implemented methods.

11. The method of claim 1, wherein the (PCR) target sequence further comprises a 16S rRNA sequence, a 23S rRNA sequence, and the region between the 16S rRNA sequence and the 23S rRNA sequence, or portions thereof.

12. The method of claim 1, wherein the one or more USID sequences are conserved in over 70% of prokaryotes.

13. The method of claim 1 wherein the genomic database is comprised of one or more rRNA gene sequences and an internally Transcribed Spacer (ITS) sequence or portions thereof.

14. A method for identifying an unknown microbe in a biological sample, comprising:
    a. selecting one or more biological samples having an unknown microbe, wherein the selecting comprises deoxyribonucleic acid (DNA) sequencing of one or more polymerase chain reaction (PCR) target sequences from whole genome DNA of the biological samples, so as to identify one or more unknown Unique DNA sequence Identifiers (USID) of the unknown microbe, wherein the (PCR) target sequence comprises a 16S rRNA sequence, a 23S rRNA sequence, and an internally Transcribed Spacer (ITS) sequence region between the 16S rRNA sequence and the 23S rRNA sequence, or a portion thereof comprising both the rRNA gene sequences and ITS sequence; wherein the identification is performed by comparing the DNA sequence results to a genomic database to ascertain whether the USID is known or unknown;

b. diluting the biological sample having the unknown microbe selected in step (a) into a high throughput format so as to enable whole genome amplification and sequencing of single microbes in the biological sample;

c. amplifying whole genome DNA from the single microbes in step (b) in a high throughput format;

d. PCR amplifying the USID sequences identified in step (a) from the genomic DNA in step (c) and detecting the presence of the unknown USID of the unknown microbe in each sample from step (c); and e. conducting DNA sequencing on the whole genome amplified DNA of the unknown microbe identified in step (d), and assembling the DNA sequences into the genome of the unknown microbe; and f. identifying the unknown microbe based on the DNA sequence of the unknown USID.

15. The method of claim 14, wherein the diluting in step (b) results in one microbe in at least one well of a multiwell plate.

16. The method of claim 14, wherein the high throughput format is selected from the group consisting of: at least six samples, at least twenty-four samples, at least forty-eight samples, or at least ninety-six samples.

17. The method of claim 16, wherein the high throughput format contains ninety-six samples.

18. The method of claim 14, wherein the biological sample is any material or fluid obtained from a human, animal, plant, or the environment.

19. The method of claim 18, wherein the biological sample is a crude biological sample or a partially-purified biological sample.

20. The method of claim 19, wherein the biological sample is selected from the group consisting of: feces, cell lysate, tissue, blood, tumor, tongue, tooth, buccal swab, phlegm, mucous, wound swab, skin swab, vaginal swab, biological material or biological fluid.

21. The method of claim 19, wherein the sample is a microbiome sample.

22. The method of claim 14, wherein the DNA sequencing in step (e) is selected from the group consisting of: a next-generation sequencing (NGS) method, Sanger sequencing or other sequencing methods.

23. The method of claim 14, wherein the assembling in step (e) employs computer implemented methods.

24. The method of claim 14, wherein the one or more USID sequences are conserved in over 70% of prokaryotes.

25. The method of claim 14 wherein the genomic database is comprised of one or more rRNA gene sequences and an internally Transcribed Spacer (ITS) sequence or portions thereof.

* * * * *